United States Patent [19]

Ducep et al.

[11] 4,075,328
[45] Feb. 21, 1978

[54] NAPHTHACENE DERIVATIVES

[75] Inventors: Jean Bernard Ducep, Paris; Daniel Farge, Thiais; Gerard Ponsinet, Sceaux; Daniel Reisdorf, Thiais, all of France

[73] Assignee: Rhone-Poulenc Industries, Paris, France

[21] Appl. No.: 695,444

[22] Filed: June 14, 1976

[30] Foreign Application Priority Data

June 16, 1975  France ............................. 75 18746

[51] Int. Cl.² ....................... A61K 31/71; C07H 15/24
[52] U.S. Cl. ...................................... 424/180; 536/4; 536/17
[58] Field of Search ..................... 536/4, 17; 424/180

[56] References Cited

U.S. PATENT DOCUMENTS 3,803,124   4/1974   Arcamone et al. ................... 536/17

OTHER PUBLICATIONS

Pigman, "The Carbohydrates," 1957, Academic Press, New York, N. Y., pp. 229–231.

Primary Examiner—Johnnie R. Brown
Attorney, Agent, or Firm—Stevens, Davis, Miller & Mosher

[57] ABSTRACT

The new naphthacene derivatives of the general formula:

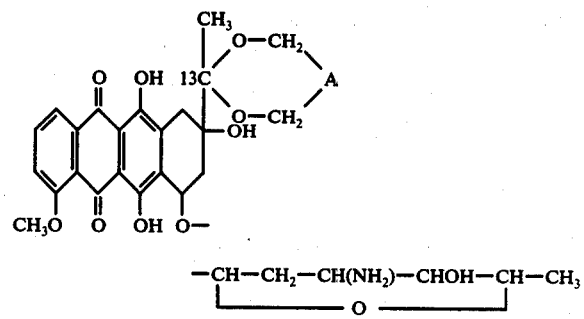

wherein A represents a single bond or a methylene group and acid addition salts thereof possess valuable anti-tumor properties. They are prepared by reaction of an acid addition salt of a strong acid of a corresponding naphthacene derivative having a

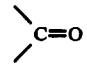

group in the 13-position with a compound of the formula HO—CH$_2$—A—CH$_2$—OH.

4 Claims, No Drawings

NAPHTHACENE DERIVATIVES

This invention relates to new naphthacene derivatives possessing anti-tumour properties, to a process for their preparation and pharmaceutical compositions containing them.

The new naphthacene derivatives of the present invention are those of the general formula:

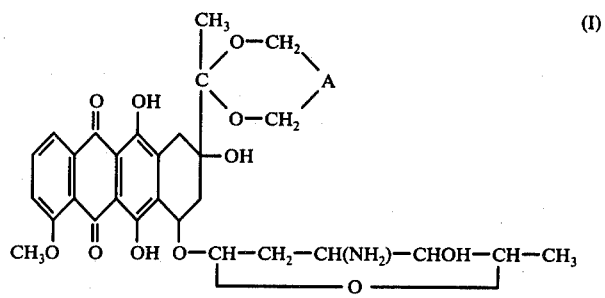

wherein A represents a single bond or a methylene group (i.e. —$CH_2$—), and acid addition salts thereof.

According to a feature of the invention, the naphthacene derivatives of general formula I are prepared by reacting a compound of the general formula:

$$HO—CH_2—A—CH_2—OH \qquad (II)$$

wherein A is as hereinbefore defined, with an acid addition salt of a strong acid, for example the hydrochloride, of a naphthacene derivative of the formula:

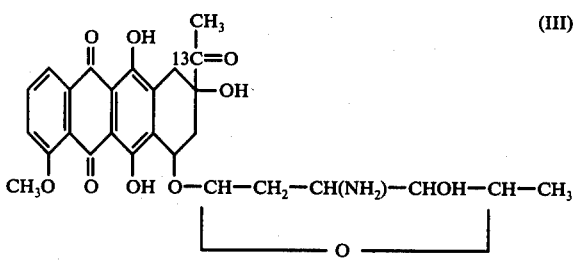

in the presence of a catalyst selected from bromine, strong mineral acids and strong organic acids, i.e. acids the pKa values of which are lower than 1.

Suitable mineral acids are, for example hydrochloric acid, hydrobromic acid, sulphuric acid and perchloric acid. Suitable organic acids are, for example trifluoroacetic acid and trichloroacetic acid, and the sulphonic acids, such as methanesulphonic acid and p-toluenesulphonic acid. If an acid catalyst is used, it may optionally be attached to a molecular sieve.

The reaction is generally carried out in an anhydrous organic solvent, e.g. dioxan, tetrahydrofuran, diglyme or 1,2-dimethoxyethane at a temperature of between 20° and 60° C.

The starting material of formula III which has been given the name "daunorubicin" is the antibiotic designated by the number 13,057 RP. The preparation of the antibiotic and of its hydrochloride, and their physicochemical characteristics are described in British patent specification No. 985,598.

The naphthacene derivatives of general formula I are the 13-ethylene- and 13-trimethylene-acetals of daunorubicin.

The naphthacene derivatives of general formula I can be purified by physical methods such as crystallisation or chromatography, or by chemical methods such as the formation of salts, crystallisation of the salts and decomposition of them in an alkaline medium. In carrying out the said chemical methods the nature of the anion of the salt is immaterial, the only requirement being that the salt must be well-defined and radily crystallisable.

The naphthacene derivatives of general formula I may be converted by methods known per se into acid addition salts. The acid addition salts may be obtained by the action of acids on the derivatives in appropriate solvents. As organic solvents there may be used alcohols, ethers, ketones or chlorinated hydrocarbons. The salt which is formed is precipitated, if necessary after concentration of the solution, and is isolated by filtration or decantation.

By the term "methods known per se" as used in this specification is meant methods heretofore used or described in the chemical literature.

The naphthacene derivatives of general formula I and their acid addition salts possess valuable pharmacological properties, in particular anti-tumour properties coupled with low toxicity.

The compounds have proved particularly active against graftable tumours in mice: at doses of between 2.5 and 10 mg./kg., administered intraperitoneally, against leukaemia L 1,210; at doses of between 1.25 and 10 mg./kg., administered intraperitoneally against leucosarcomatosis; at doses of between 0.5 and 5 mg./kg., administered intraperitoneally, against leukaemia P 388; at a dose of 5 mg./kg., administered intraperitoneally, against grafted benzopyrene sarcoma, and at a dose of 10 mg./kg., administered subcutaneously, against sarcoma 180.

Their sub-acute 50% lethal dose ($LD_{50}$) determined in mice, using one administration per day for 5 days, is between 10 and 25 mg./kg. for intraperitoneal administration.

For therapeutic purposes, the naphthacene derivatives of general formula I may be employed as such or in the form of non-toxic acid addition salts, i.e. salts containing anions which are relatively innocuous to the animal organism in therapeutic doses of the salts (such as hydrochlorides, sulphates, nitrates, phosphates, acetates, propionates, succinates, benzoates, fumarates, maleates, tartrates, theophyllinacetates, salicylates, phenolphthalinates and methylene-bis-β-hydroxynaphthoates) so that the beneficial physiological properties inherent in the bases are not vitiated by side effects ascribable to the anions.

The following Examples illustrate the invention.

EXAMPLE 1

Daunorubicin hydrochloride (3 g.) is dissolved in ethylene glycol (75 cc.). Dioxan (240 cc.) is added to the solution, which is stirred at 20° C., and a solution of bromine (0.75 g.) in chloroform (7 cc.) is added over the course of one minute. Stirring is continued for 4 hours at 20° C. Water (300 cc.) is then added and the mixture is extracted with chloroform (3 × 200 cc.). The aqueous phase is brought to pH 8 by adding sodium bicarbonate, then extracted with chloroform (4 × 200 cc.). These four chloroform extracts are combined, washed with water, dried over sodium sulphate, filtered and concentrated to dryness under reduced pressure (1 mg Hg at 30° C. and then 0.1 mm. Hg at 20° C.).

Daunorubicin-13-ethylene-acetal (1.7 g.) is obtained.
Rf = 0.48 [silica gel; methylene chloride/methanol/formic acid/water (88/15/2/1 by volume)].
$[\alpha]_D^{20} = 218° \pm 32°$ (c = 0.1, methanol).

EXAMPLE 2

A 0.19N solution (18.5 cc.) of dry hydrogen chloride in dioxan is added to a stirred solution of daunorubicin hydrochloride (20 g.) in a mixture of dioxan (1,600 cc.) and ethylene glycol (500 cc.).

The mixture is heated for 8 hours at 35° C. and then for 4 hours at 40° C. After cooling to 20° C., the reaction mixture is poured into a 5% (w/v) aqueous sodium bicarbonate solution (1 liter). The mixture is extracted with diethyl ether (5 × 500 cc.) and then with chloroform (5 × 400 cc.). The chloroform extracts are combined, dried over sodium sulphate, filtered and concentrated to dryness under reduced pressure (1 mm Hg) at 30° C.

The product obtained is dissolved in 0.05M aqueous hydrochloric acid. The solution is extracted with chloroform (3 × 50 cc.), then brought to pH 8 by adding sodium bicarbonate and extracted with chloroform (5 × 200 cc.). These five chloroform extracts are combined, dried over sodium sulphate, filtered and concentrated to dryness under reduced pressure (1 mm Hg at 30° C., and then 0.1 mm Hg at 20° C.).

Daunorubicin-13-ethylene-acetal (5.8 g.) is obtained, the characteristics of which are identical to those of the product of Example 1.

EXAMPLE 3

A 0.98N solution (9.7 cc.) of dry hydrogen chloride in dioxan is added to a solution, which is stirred at 0° C., of daunorubicin-13-ethylene-acetal (5.7 g.) in methylene chloride (50 cc.). The precipitate obtained is filtered off and washed with methylene chloride (3 × 10 cc.) at 5° C. The product is dried at 40° C. under reduced pressure (0.1 mm Hg) in the presence of phosphorus pentoxide.

Daunorubicin-13-ethylene-acetal hydrochloride (4.2 g.) is obtained as a red powder which is soluble in water and in methanol.

$[\alpha]_D^{20} = +95° \pm 4°$ (c = 1, methanol).

Elementary Analysis: Calculated: C 57.3%: H 5.6%: Cl 5.8%: N: 2.3%: O: 28.9%. Found: C 55.2%: H 6.1%: Cl 5.5%: N 23%: O: 29.6%.

EXAMPLE 4

Daunorubicin hydrochloride (10 g.) is dissolved in propane-1,3-diol (250 cc.), and dioxan (800 cc.) and a 0.49N solution (7.5 cc.) of dry hydrogen chloride in dioxan are then added. After 4 days at 20° C., a 5% (w/v) aqueous sodium bicarbonate solution (1 liter) is added. The mixture is extracted with chloroform (5 × 200 cc.). The chloroform extracts are combined, dried over sodium sulphate, filtered and concentrated to 100 cc. under reduced pressure (25 mm Hg) at 30° C. The solution obtained is diluted with diethyl ether (500 cc.). The precipitate formed is filtered off, washed with diethyl ether and dried at 20° C. under reduced pressure (1 mm Hg).

The product obtained is dissolved in chloroform (50 cc.) and the solution poured onto a column of silica gel (200 g.) in chloroform. The column is eluted with chloroform (1 liter) andd then with a mixture of chloroform and ethyl acetate (94-6 by volume; 5 liters), the eluate being collected in fractions of 100 cc. Fractions No. 20 to 40, which contain a mixture of daunorubicin and daunorubicin-13-trimethylene-acetal, are combined and concentrated to dryness under reduced pressure (25 mm Hg) at 30° C.

The product obtained is dissolved in a mixture containing water (300 cc.), methanol (100 cc.), aminooxyacetic acid (semi-hydrochloride) (4.4 g.) and sodium acetate trihydrate (5.4 g.). The mixture is left for 18 hours at 20° C. and is then extracted with chloroform (5 × 100 cc.). The chloroform extracts are combined, dried over sodium sulphate and concentrated to dryness under reduced pressure (25 mm Hg) at 30° C. Crude daunorubicin-13-trimethylene-acetal (2.1 g.) is thus obtained. This product (0.1 g.) is dissolved in tetrahydrofuran (3 cc.) and diethyl ether (10 cc.) is added. The red precipitate obtained is filtered off, washed with diethyl ether and dried at 40° C. under reduced pressure (0.1 mm Hg).

Daunorubicin-13-trimethylene-acetal (0.080 g.) is thus obtained.

$[\alpha]_D^{20} = +71° \pm 6°$ (c = 0.5, methanol)

Elementary analysis: Calculated: C 61.53%: H 6.02%: N 2.39%. Found: C 62.3%: H 6.5%: N 2.5%.

EXAMPLE 5

Daunorubicin-13-trimethylene-acetal (2 g.) is dissolved in methylene chloride (20 cc.); a 0.49N solution (7.1 cc.) of dry hydrogen chloride in dioxan is added, followed by diethyl ether (400 cc.). The precipitate formed is filtered off, washed with diethyl ether and dried under reduced pressure (0.1 mm Hg) at 40° C. Daunorubicin-13-trimethylene-acetal hydrochloride (1.85 g.) is thus obtained.

$[\alpha]_D^{20} = +123° \pm 7°$ (c = 0.5, methanol).

The present invention includes within its scope pharmaceutical compositions comprising, as active ingredient, at least one of the naphthacene derivatives of general formula I, or a non-toxic acid addition salt thereof, in association with a compatible pharmaceutically acceptable carrier and/or a compound which may itself be physiologically active, for example an antibiotic. The compositions may be made up in any pharmaceutical form appropriate for the route of administration in question. The preferred method of administration is parenteral administration, especially intravenous administration.

Preparations according to the invention for parenteral administration include sterile aqueous or non-aqueous solutions, suspensions or emulsions. Examples of non-aqueous solvents or vehicles are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilized, for example, by filtration through a bacteria-retaining filter, by incorporation in the compositions of sterilizing agents, by irradiation, or by heating. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage shall be obtained. The dosage depends on the desired therapeutic effect, on the route of administration and on the duration of the treatment. The compositions of the invention are particularly useful in the treatment of cancers. In human therapy the compositions when administered intravenously to an adult should generally give doses between 2 mg. and 4 mg./kg. of active substance per day. In general the physician will decide the posology considered appropriate, taking into account the age and weight and other factors intrinsic to the patient being treated.

The following Example illustrates pharmaceutical compositions according to the invention.

EXAMPLE 6

A solution containing daunorubicin-13-ethylene-acetal hydrochloride (31.9 mg./cc.) is prepared by dissolving the hydrochloride (3.19 g.) in a sufficient amount of a non-pyrogenic physiological solution to give 100 cc. The solution obtained is divided aseptically between ampoules at the rate of 5 cc. per ampoule. The ampoules, each containing daunorubicin-13-ethylene-acetal (150 mg. expressed as free base), are sealed.

We claim:

1. The naphthacene derivative of the formula:

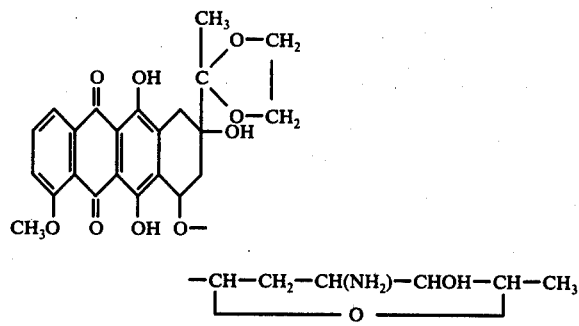

and non-toxic acid addition salts thereof.

2. Daunorubicin-13-ethylene-acetal.

3. Daunorubicin-13-ethylene-acetal hydrochloride.

4. A pharmaceutical composition which comprises as active ingredient a significant amount of the naphthacene derivative or non-toxic acid addition salt thereof as claimed in claim 1 in association with a compatible pharmaceutically acceptable carrier.